United States Patent
Inazawa et al.

(10) Patent No.: US 9,229,003 B2
(45) Date of Patent: Jan. 5, 2016

(54) METHOD FOR DETECTING THYROID CARCINOMA

(75) Inventors: Johji Inazawa, Tokyo (JP); Issei Imoto, Tokyo (JP); Takaya Ishihara, Tokyo (JP); Hitoshi Tsuda, Tokyo (JP)

(73) Assignees: FUJIFILM Corporation, Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 39 days.

(21) Appl. No.: 12/503,434

(22) Filed: Jul. 15, 2009

(65) Prior Publication Data

US 2010/0035262 A1     Feb. 11, 2010

(30) Foreign Application Priority Data

Jul. 16, 2008  (JP) ................. 2008-184982

(51) Int. Cl.
*C12Q 1/68* (2006.01)
*C12Q 1/70* (2006.01)
*C12P 19/34* (2006.01)
*G01N 33/574* (2006.01)

(52) U.S. Cl.
CPC ........ *G01N 33/57407* (2013.01); *C12Q 1/6886* (2013.01); *C12Q 2600/112* (2013.01); *C12Q 2600/156* (2013.01)

(58) Field of Classification Search
None
See application file for complete search history.

(56) References Cited

PUBLICATIONS

Roque et al. (Genes Chromosome and cancer 2003 vol. 36 p. 292).*
Izzi et al. (Neoplasia 2006 vol. 8 p. 677).*
Ishihara et al. (Cancer Science Oct. 2008 vol. 99 p. 1940).*
Staub et al. (Molecular Cancer 2006 vol. 5 p. 1-44).*
Heldin et al. (Molecular and Cellular Endocrinology 1999 vol. 153 p. 79).*
Courbard et al. (Journal of Biological Chemistry 2002 vol. 277 p. 45267).*
Enard et al. (Science 2002 vol. 296 p. 340).*
Cobb et al (Crit Care Med 2002 vol. 30 p. 2711).*
Cheung et al (Nature Genetics 2003 vol. 33 p. 422).*
Wu (Journal of pathology 2001 vol. 195 p. 53).*
Newton et al (Journal of Computational Biology 2001 vol. 8 p. 37).*
Japanese Office Action for Japanese Application No. 2008-184982, mailed Aug. 6, 2013, along with an English translation thereof.
Inazawa et al., "Comparative genomic hybridization (CGH)-arrays pave the way for identification of novel cancer-related genes," Cancer Sci., vol. 95, No. 7, Jul. 2004, pp. 559-563.
Japanese Office Action, dated May 14, 2013, for Japanese Application No. 2008-184982, with partial English translation.
Mori et al., "Detection of numerical abberations on chromosome 17 in human thyroid tumors," J. Jpn. Soc. Clin. Cytol., vol. 33, No. 6, Nov. 1994, pp. 1167-1168.

* cited by examiner

*Primary Examiner* — Katherine Salmon
(74) *Attorney, Agent, or Firm* — Birch, Stewart, Kolasch & Birch, LLP

(57) ABSTRACT

It is an object of the present invention to identify a gene that exhibits behavior which is characteristic of carcinomas such as thyroid carcinoma, so as to provide a method for detecting carcinoma and a cell growth suppressing agent. The present invention provides a method for detecting carcinoma, which comprises detecting malignant transformation by detecting at least one alteration of gene existing in chromosomal regions 1q41, 3q28, 7q31.2, 8p12, 8q22.2, 8q24.21, 11q4.1, 17q12, 20q11, 9p21.3, 16q13.2, and 16q23.1 in a specimen.

1 Claim, 8 Drawing Sheets

METHOD FOR DETECTING THYROID CARCINOMA

TECHNICAL FIELD

The present invention relates to a method for detecting carcinoma, which comprises detecting alteration of gene that exists in the specific chromosomal regions of a specimen.

BACKGROUND ART

Anaplastic thyroid carcinoma (hereinafter referred to as "ATC") accounts for 2% to 5% of thyroid carcinoma, and it is one type of carcinoma having an extremely high degree of malignancy. Well-differentiated thyroid carcinoma (WDTC), namely, papillary thyroid carcinoma (PTC) and follicular thyroid carcinoma have a good prognosis. In contrast, ATC is considered as a solid cancer having an extremely poor prognosis. The median survival period of ATC is said to be 4 to 12 months. It has been known that ATC shares several genetic abnormalities with WDTC (point mutations of RAS gene and BRAF gene, point mutation or gene amplification of PIK3CA gene, etc.). On the other hand, mutation of a TP53 gene rarely occurs in WDTC, but it has been known that TP53 gene has been mutated in 70% or more of ATC. Based on the histological correlation of ATC with WDTC, it has been considered that ATC develops from WDTC serving as a previous stage. However, several types of ATCs newly develop (de novo ATC). Thus, under the current circumstances, the molecular mechanism of ATC in terms of the degree of malignancy has hardly been clarified.

As a result of recent progress in molecular-targeted therapy for cancer genes, it is considered that detailed clarification of the mutated regions of gene in ATC leads to the development of an effective therapy.

A change in the copy number of a gene, such as amplification or homozygous deletion, becomes a marker useful in identifying cancer genes causing malignant transformation or cancer-suppressing genes.

The present inventors had analyzed various cancer cell lines using a conventional high throughput array CGH method, so that they had accomplished identification of new genes that cause malignant transformation. The inventors had analyzed ATC using MCG Cancer Array800 (Yu et al., Oncogene 26, 1178-1187, 2007) as one type of high throughput array. As a result, they had discovered a DUSP26 gene acting as a novel marker gene. However, clarification of the molecular mechanism of ATC has been still insufficient, and thus further analyses have been desired.

DISCLOSURE OF THE INVENTION

If the mechanism of malignant transformation of ATC having a particularly poor prognosis among thyroid tumors were clarified at a genetic level, it would enable the early discovery of malignant transformation of thyroid gland-derived cells at a genetic level, the diagnosis of degree of malignancy of thyroid carcinoma, and suppression of cancer progression. Moreover, it would further enable selection of a drug based on such mechanism, the development of a therapeutic drug, and the establishment of therapy. Specifically, it is considered that the aforementioned problems can be solved by identifying a gene that exhibits behavior which is characteristic of anaplastic thyroid carcinoma and then performing technical analyses on the gene and others. That is to say, it is an object of the present invention to identify a gene that exhibits behavior which is characteristic of carcinomas such as thyroid carcinoma, so as to provide a method for detecting carcinoma and a cell growth suppressing agent.

Comparative Genomic Hybridization (CGH) is the best method for conveniently and rapidly analyzing genetic abnormalities accompanying amplification or deletion of numerous genes in the genome or inactivation of genes. In order to analyze genetic abnormalities in the genome involved in malignant transformation and higher cancer malignancy, the present inventors have selected 4500 types of BAC/PAC DNA to be subjected to a CGH array (MCG Whole Genome-4500; Inazawa J., et al., Cancer Sci. 95, 559-563, 2004). As a result, the present inventors have discovered 12 characteristic chromosomal regions that alter in thyroid carcinoma (1q41, 3q28, 7q31.2, 8p12, 8q22.2, 8q24.21, 11q14.1, 17q12, 20q11, 9p21.3, 16q13.2, and 16q23.1), and they have also discovered 9 cancer-associated genes, which promote the malignant transformation of thyroid gland-derived cells (an ITCH gene, an AHCY gene, a DYNLRB1 gene, an MAP1LC3A gene, a PIGU gene, a TP531PN2 gene, an NCOA6 gene, an HMG4L gene, and an ASIP1 gene). Also, the inventors have succeeded in identifying a new copy number abnormality of 20q11 comprising the ITCH (itchy homolog E3 ubiquitin protein ligase) gene that is particularly preferable as a marker. Moreover, the inventors have clarified excessive expression of an ITCH protein in primary thyroid carcinoma including ATC by immunohistorical analyses. Further, the inventors have succeeded in discovering that an increase in the ITCH protein significantly promotes the growth of ATC cells, and that the growth of ATC cells is significantly reduced if the transcription product of the ITCH gene is suppressed, thereby completing the present invention.

The present invention provides a method for detecting carcinoma, which comprises detecting malignant transformation by detecting at least one alteration of gene existing in chromosomal regions 1q41, 3q28, 7q31.2, 8p12, 8q22.2, 8q24.21, 11q14.1, 17q12, 20q11, 9p21.3, 16q13.2, and 16q23.1 in a specimen.

Preferably, at least one amplification of gene existing in chromosomal regions 1q41, 3q28, 7q31.2, 8p12, 8q22.2, 8q24.21, 11q14.1, 17q12, and 20q11 and/or at least one deletion of gene existing in chromosomal regions 9p21.3, 16q13.2, and 16q23.1 is detected.

Preferably, amplification of gene existing in chromosomal region 20q11 is detected in a specimen.

Preferably, the gene is at least one selected from among ITCH, AHCY, DYNLRB1, MAP1LC3A, PIGU, TP531PN2, NCOA6, HMG4L, and ASIP1.

Preferably, as an indicator of amplification, the amplification rate of the specimen is higher than that of a normal specimen by a factor of 1.32 or more.

Preferably, the gene is an ITCH gene.

Preferably, the specimen is a tissue derived from the thyroid gland.

Preferably, the carcinoma is thyroid carcinoma.

Preferably, the gene alteration is detected using a DNA chip method, a Southern blot method, a Northern blot method, a real-time RT-PCR method, a FISH method, a CGH method, an array CGH method, a bisulfite sequencing method, or a COBRA method.

The present invention further provides a method for detecting carcinoma, which comprises detecting the amount of a protein translated from at least one gene selected from among ITCH, AHCY, DYNLRB1, MAP1LC3A, PIGU, TP531PN2, NCOA6, HMG4L, and ASIP1 in a specimen.

Preferably, the amount of a protein is detected by an immunohistochemical method.

Preferably, malignant transformation including the degree of malignancy of the specimen is detected.

The present invention further provides a method for suppressing cell growth, which comprises introducing into cells in vitro an siRNA, an antisense oligonucleotide or a loss-of-function type gene of at least one gene selected from among ITCH, AHCY, DYNLRB1, MAP1LC3A, PIGU, TP53I1PN2, NCOA6, HMG4L, and ASIP1.

The present invention further provides a cell growth suppressing agent, which comprises an siRNA, an antisense oligonucleotide or a loss-of-function type gene of at least one gene selected from among ITCH, AHCY, DYNLRB1, MAP1LC3A, PIGU, TP53I1PN2, NCOA6, HMG4L, and ASIP1.

The present invention further provides a method for activating cell growth, which comprises introducing into cells in vitro at least one gene selected from among ITCH, AHCY, DYNLRB1, MAP1LC3A, PIGU, TP53I1PN2, NCOA6, HMG4L, and ASIP1.

The present invention further provides a cell growth activating agent, which comprises at least one gene selected from among ITCH, AHCY, DYNLRB1, MAP1LC3A, PIGU, TP53I1PN2, NCOA6, HMG4L, and ASIP1.

According to the present invention, it has become possible to precisely understand the malignant transformation and the malignancy degree in a thyroid gland-derived cell specimen. Furthermore, proliferation of thyroid carcinoma, and particularly anaplastic thyroid carcinoma, can be suppressed by introducing the transcription product of the gene of the present invention that inactivates gene expression into the thyroid carcinoma.

BRIEF DESCRIPTION OF DRAWING

FIG. 1 shows amplification and excessive expression of the ITCH genes of ATC cell lines.

FIG. 3(C) shows cell number distribution at each cell cycle measured by FACS 72 hours after introduction of siRNA-ITCH and siRNA-Luc into 8305C cells. The figure shows that G0/G1-phase cells are accumulated by introduction of ITCH-specific siRNA.

PREFERRED EMBODIMENT OF THE INVENTION

Figure 1A:
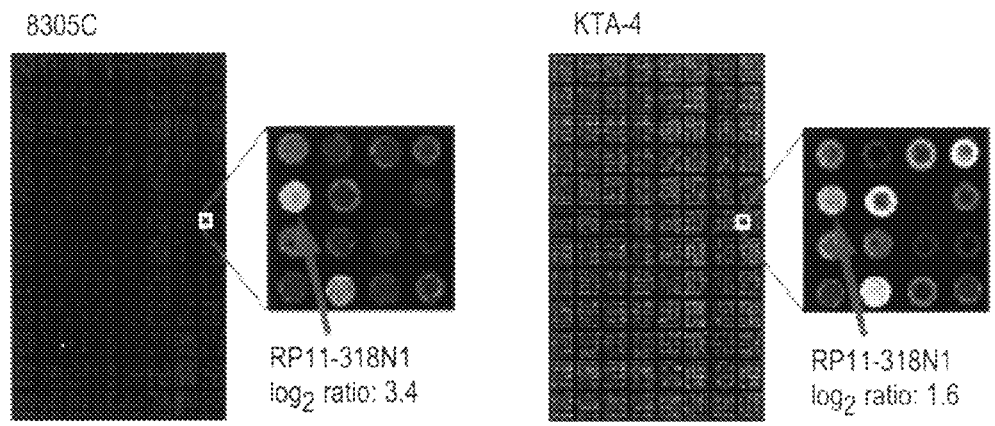
FIG. 1(A) shows array CGH analysis images obtained using MCG Whole Genome Array-4500. A significant increase in the copy number was detected as a clear green signal in the 20q11.22 region in two ATC cell lines (a 8305C cell line and a KTA-4 cell line) (red arrows).

Hereafter, the present invention will be described more in detail.

(1) Method for Detecting Carcinoma

The method for detecting carcinoma according to the present invention is characterized in that it comprises detecting at least one alteration of gene existing in chromosomal regions 1q41, 3q28, 7q31.2, 8p12, 8q22.2, 8q24.21, 11q14.1, 17q12, 20q11, 9p21.3, 16q13.2, and 16q23.1 in a specimen. Preferably, a gene to be detected is an ITCH gene.

The ITCH gene (itchy homolog E3 ubiquitin protein ligase) is also referred to as AIP4 (atrophin-1 interacting protein 4), and it belongs to Nedd4-like protein family which is E3 ubiquitin ligase. The ITCH gene has a structure in which a C2 region relating to protein kinase-C exists on the N-terminal side and four WW regions and an HECT (homologous to the E6-associated protein carboxyl-terminus) ubiquitin protein ligase region exist on the C-terminal side. A mouse having no Itch gene (Itchy) exhibits fetal symptoms attended with constant itching of the skin, severe inflammation, and immunodeficiency. It is considered that Nedd4-like E3 plays an important role in the carcinogenesis of esophageal squamous cell carcinoma, breast carcinoma, prostatic carcinoma, and pancreatic carcinoma. However, there have been almost no reports regarding the relationship between the ITCH gene and carcinoma.

As described above, the present detection method is characterized in that it comprises detecting mutation of the chromosomal regions of the present invention and the multiple genes of the present invention in thyroid gland-derived cells or in thyroid carcinoma.

Preferred examples of thyroid gland-derived cells or thyroid carcinoma to be subjected to detection of mutation of the chromosomal regions of the present invention and the multiple genes of the present invention include biopsied tissue cells of specimen donors.

Such biopsied tissue cells of specimen donors may be either the thyroid gland-derived cells of a healthy subject or the cancerous tissues of a thyroid carcinoma patient. In practice, examples of a major target tissue specimen that can be used herein include: a tissue obtained from a lesion in which suspected malignant transformation is observed by a test or the like; and a thyroid carcinoma tissue that has been confirmed to be derived from thyroid carcinoma and thus must be subjected to determination of malignancy or the stage progression of the thyroid carcinoma.

When the mutation of the chromosomal regions of the present invention and the multiple genes of the present invention is confirmed by the method of the present invention in the "pathologic tissue of thyroid glands having a lesion suspected to be malignant as confirmed by a test or the like", it is revealed that the pathologic tissue is undergoing a process toward canceration or is already in the malignant state, and that the malignancy thereof is increasing. Thus, the need to carry out immediate full-scale treatment (such as lesion removal by operation or the like and full-scale chemotherapy) is demonstrated. Moreover, when the mutation of the chromosomal regions of the present invention and the multiple genes of the present invention is confirmed in the "tissue that is confirmed to be thyroid carcinoma and for which determination of malignancy or the stage progression thereof is required", it is revealed that the malignancy of the cancer tissue is increasing. Hence, the need to carry out immediate full-scale treatment (such as lesion removal by operation or the like or full-scale chemotherapy) is demonstrated. A thyroid carcinoma tissue sampled as a specimen can be subjected to the present detection method after applying necessary treatment such as with the preparation of DNA or RNA from the sampled tissue.

In the detection method of the present invention, the mutation of the chromosomal regions of the present invention and the multiple genes of the present invention is detected in thyroid gland-derived cells or thyroid carcinoma cells as mentioned above, so that tumorigenic transformation of said cells is detected and classified.

Next, detection of the mutation of the chromosomal regions of the present invention and the multiple genes of the present invention is described below.

Examples of a typical method by which amplification or deletion of the chromosomal regions of the present invention and the multiple genes of the present invention can be directly detected include a CGH (Comparative Genomic Hybridization) method and a FISH (Fluorescence in situ hybridization) method. According to the detection method in this embodiment, BAC (Bacterial Artificial Chromosome) DNA, YAC (Yeast Artificial Chromosome) DNA, or PAC (P1-drived Artificial Chromosome) DNA (hereinafter, also referred to as BAC DNA, for example) having the chromosomal regions of the present invention and the multiple genes of the present invention is labeled and then FISH is performed, so that the presence or the absence of the chromosomal regions of the present invention and the multiple genes of the present invention can be detected.

It is preferable and practical to carry out the method in the above embodiment with the use of a genomic DNA-immobilized matrix.

The amount of BAC DNA or the like obtained in a conventional manner is so small that a large number of genomic DNA-immobilized matrices cannot be produced for practical application. Thus, it is necessary to obtain gene amplification products of such DNA. (A gene amplification process for this purpose is referred to as "infinite amplification" in some cases.) Upon infinite amplification, BAC DNA or the like is first digested with a four-base recognition enzyme such as Rsa I, Dpn I, Hae III, or the like, followed by ligation with the addition of an adaptor. An adaptor comprises oligonucleotides having 10 to 30 bases and preferably 15 to 25 bases. Double strands of such adaptor have sequences complementary to each other. After annealing, the 3' end of one of the oligonucleotides, at which a blunt end is formed, must be phosphorylated. Next, a primer having a sequence identical to the other oligonucleotide of the adaptor is used for amplification via PCR (polymerase chain reaction). Thus, infinite amplification can be carried out. Meanwhile, it is also possible to use, as a detection probe, an aminated oligonucleotide comprising 50 to 70 bases, which is inherent to BAC DNA or the like.

BAC DNAs or the like subjected to infinite amplification are immobilized on a matrix and preferably on a solid matrix. Accordingly, a desired DNA-immobilized matrix can be produced. An example of such solid matrix is more preferably a glass plate. Such a solid matrix made of glass or the like is more preferably coated via adhesion with poly-L-lysine, aminosilane, gold, aluminium, or the like.

The concentration of DNA subjected to infinite amplification to be spotted on a matrix is preferably 10 pg/µl to 5 µg/µl and more preferably 1 ng/µl to 200 ng/µl. The amount of the same to be spotted on the matrix is preferably 1 nl to 1 µl and more preferably 10 nl to 100 nl. In addition, the size and the shape of each spot that is immobilized on the matrix are not particularly limited. In terms of size, such spot may have a diameter ranging from 0.01 to 1 mm, for example. In addition, the shape of such spot may be a circle or ellipse from an overhead view. The thickness of a dry spot is not particularly limited; however, it may be 1 to 100 µm. Further, the number of spots is not particularly limited; however, it may be 10 to 50,000 spots and more preferably 100 to 5,000 spots on the matrix used. DNAs are spotted singly to quadruplicate. However, preferably, DNAs are spotted in duplicate or triplicate.

Regarding preparation of dry spots, it is possible to produce dry spots by, for example, spotting BAC DNAs or the like subjected to infinite amplification on a matrix with the use of a spotter, forming a plurality of spots thereon, and drying the spots. Examples of a spotter that can be used include an inkjet printer, a pin-array printer, and a bubble jet (trademark) printer. An inkjet printer is desirably used. For instance, GENESHOT (NGK INSULATORS; Nagoya, Japan) or the like can be used.

As described above, it is possible to produce a desired DNA-immobilized matrix by immobilizing BAC DNAs or the like subjected to infinite amplification onto a matrix, and preferably, onto a solid matrix.

In addition, an example of a means of directly detecting the deletion of the chromosomal regions of the present invention and the multiple genes of the present invention is the Southern blot method. The Southern blot method is a method for detecting the presence of the chromosomal regions of the present invention and the multiple genes of the present invention in a specimen by separating and immobilizing genomic DNA obtained from the specimen and detecting hybridization of such genomic DNA with the chromosomal regions of the present invention and the multiple genes of the present invention.

Furthermore, the amplification of the chromosomal regions of the present invention and the multiple genes of the present invention can also be directly detected by the PCR method. Genomic DNA is separated from a test sample, and is amplified using a primer which can amplify a full length of said gene or a part thereof, and the amplified product is quantified so that the amplification of the gene can be detected.

In the present invention, malignant transformation including the degree of malignancy of the specimen can be detected by detecting at least one alteration of gene existing in chromosomal regions 1q41, 3q28, 7q31.2, 8p12, 8q22.2, 8q24.21, 11q14.1, 17q12, 20q11, 9p21.3, 16q13.2, and 16q23.1.

With regard to detection of mutation, mutation is preferably detected in chromosomal regions 1q41, 3q28, 7q31.2, 8p12, 8q22.2, 8q24.21, 11q14.1, 17q12, and 20q11, whereas deletion is preferably detected in chromosomal regions 9p21.3, 16q13.2, and 16q23.1.

It is more preferable to use gene amplification of the 20q11 region in a specimen as an indicator. It is further preferable to detect at least one mutation of gene selected from among genes in the 20q11 region, namely, ITCH, AHCY, DYNLRB1, MAP1LC3A, PIGU, TP531PN2, NCOA6, HMG4L, and ASIP1, and to detect malignant transformation including the degree of malignancy of the specimen.

In addition, it is preferable that, as an indicator of amplification, the amplification rate of the specimen be higher than that of a normal specimen by a factor of 1.32 or more.

It is particularly preferable to use the gene amplification of the ITCH gene as an indicator.

Moreover, the specimen is preferably a tissue derived from thyroid gland, and more preferably thyroid carcinoma.

Specifically, in a method for detecting mutation of the chromosomal region 1q41, RP11-124A11, RP11-5F19, RP11-79H5, RP11-45L21, RP11-66M7, or the like is preferably used as BAC-DNA. In a method for detecting mutation of the chromosomal region 3q28, RP11-54L9, RP11-455C22, RP11-88H6, or the like is preferably used as BAC-DNA. In a method for detecting mutation of the chromosomal region 7q31.2, RP11-51M22 or the like is preferably used as BAC-DNA. In a method for detecting mutation of the chromosomal region 8p12, RP11-451018, RP11-258M15, RP11-91P13, or the like is preferably used as BAC-DNA. In a method for detecting mutation of the chromosomal region 8q22.2, RP11-142F22 or the like is preferably used as BAC-DNA. In a method for detecting mutation of the chromosomal region 8q24.21, RP11-89K10, RP11-89L16, or the like is preferably used as BAC-DNA. In a method for detecting mutation of the chromosomal region 11q14.1, RP11-91M10 or the like is preferably used as BAC-DNA. In a method for detecting mutation of the chromosomal region 17q12, RP11-19G24 or the like is preferably used as BAC-DNA. In a method for detecting mutation of the chromosomal region 20q11, RP11-318N1 or the like is preferably used as BAC-DNA.

Moreover, in a method for detecting mutation of the chromosomal region 9p21.3, RP11-113D19, RP11-344A7, RP11-408N14, RP11-44115, RP-11-11J1, RP11-782K2, RP11-346N23, RP11-33015, RP11-482110, or the like is preferably used as BAC-DNA. In a method for detecting mutation of the chromosomal region 16q13.2, RP11-185J20 or the like is preferably used as BAC-DNA. In a method for detecting mutation of the chromosomal region 16q23.1, RP11-61L1 or the like is preferably used as BAC-DNA.

Furthermore, an example of BAC-DNA having an ITCH gene that is the most preferable marker gene is RP11-318N1.

For handling the multiple genes of the present invention, cDNAs obtained from cultured cells through publicly known methods to those skilled in the art may be used, or enzymatically synthesized ones through PCR method may be also used. When DNA having a known nucleotide sequence is obtained through PCR method, PCR is performed using human chromosomal DNA or cDNA library as a template, and primers designed to amplify a nucleotide sequence of interest. DNA fragments amplified through PCR can be cloned in an appropriate vector which can proliferate in a host such as E. coli.

Manipulations such as preparation of detection probes or primers for the chromosomal regions of the present invention and the multiple genes of the present invention and cloning of target genes are already known to those skilled in the art. For example, such manipulations can be performed according to methods described in Molecular Cloning: A Laboratory Manual, $2^{nd}$ Ed., Cold Spring Harbor Laboratory, Cold Spring Harbor, N.Y., 1989, Current Protocols in Molecular Biology, Supplement 1 to 38, John Wiley & Sons (1987-1997), or the like.

(2) Method for Suppressing Cell Growth and Cell Growth Suppressing Agent

According to the present invention, there are provided a method for suppressing cell growth which comprises introducing an siRNA, an shRNA, an antisense oligonucleotide, or a loss-of-function type gene of the ITCH, AHCY, DYNLRB1, MAP1LC3A, PIGU, TP531PN2, NCOA6, HMG4L, and ASIP1 into cells in vitro, and a cell growth suppressing agent which comprises said siRNA, shRNA, antisense oligonucleotide, or loss-of-function type gene.

siRNA is a double-strand RNA having a length of about 20 nucleotides (for example, 21 to 23 nucleotides) or shorter. Expression of such an siRNA in a cell enables to suppress the expression of a gene targeted by the siRNA (ITCH, AHCY, DYNLRB1, MAP1LC3A, PIGU, TP531PN2, NCOA6, HMG4L, or ASIP1 gene in the present invention).

The siRNA to be used in the present invention may take any form as long as it is capable of inducing RNAi. Here, the term "siRNA" is an abbreviation for "short interfering RNA", which refers to a short-chain double-strand RNA of 10 nucleotides or longer obtained by: chemical or biochemical synthesis in an artificial manner; in vivo synthesis; or in vivo degradation of double-strand RNA of about 40 nucleotides or longer. The siRNA normally has a structure comprising 5'-phosphoric acid and 3'-OH, where the 3' terminal projects by about 2 nucleotides. A specific protein binds to the siRNA to form RISC(RNA-induced-silencing-complex). This complex recognizes mRNA having the homologous sequence to that of siRNA and binds thereto. Then, the mRNA is cleaved at the central part of the siRNA with an RNase III-like enzymatic activity.

The siRNA sequence and the mRNA sequence being the target of cleavage preferably match 100%. However, such 100% match is not always required, when unmatched nucleotides are located away from the central part of the siRNA. This is because the RNAi cleaving activity often partially remains.

Preferably, the homologous region between the siRNA nucleotide sequence and the nucleotide sequence of the ITCH, AHCY, DYNLRB1, MAP1LC3A, PIGU, TP531PN2, NCOA6, HMG4L, or ASIP1 gene whose expression has to be suppressed, does not include the translation initiation region of the concerned gene. Since various transcriptional factors and translational factors are predicted to bind to the translation initiation region, it is anticipated that the siRNA be unable to effectively bind to the mRNA, leading to lowered effect. Accordingly, the homologous sequence is preferably away from the translation initiation region of the concerned gene by 20 nucleotides, and more preferably by 70 nucleotides. The homologous sequence may be, for example, a sequence in the vicinity of the 3' terminal of the concerned gene.

According to another aspect of the present invention, an shRNA (short hairpin RNA) comprising a short hairpin structure having a projection at the 3' terminal may also be used as a factor which can suppress the expression of a target gene through RNAi. The term shRNA refers to a molecule of about 20 or more nucleotides, in which the single-strand RNA includes partially palindromic nucleotide sequences to thereby have a double-strand structure within the molecule, forming a hairpin-like structure. Such an shRNA is broken down into a length of about 20 nucleotides (typically 21 nucleotides, 22 nucleotides, and 23 nucleotides, for example) within a cell after being introduced into the cell, and thus is capable of inducing RNAi in a similar manner to that of siRNA. As described above, the shRNA induces RNAi in a similar manner to that of siRNA, and thus can be effectively used in the present invention.

The shRNA preferably has a projection at the 3' terminal. There is no particular limitation on the length of the double-strand portion, although it is preferably about 10 or more nucleotides, and more preferably about 20 or more nucleotides. Here, the projecting 3' terminal is preferably a DNA, more preferably a DNA of at least 2 or more nucleotides, and yet more preferably a DNA of 2 to 4 nucleotides.

As described above, in the present invention, siRNA or shRNA can be used as a factor which can suppress the expression of the ITCH, AHCY, DYNLRB1, MAP1LC3A, PIGU, TP531PN2, NCOA6, HMG4L, or ASIP1 gene through RNAi. The advantages of siRNA are such that: (1) RNA itself, even when introduced into a cell, is not incorporated into a chromosome of normal cell, and therefore the treatment do not cause any inheritable mutations and the safety is high; (2) it is relatively easy to chemically synthesize short-chain double-strand RNA, and the form of double-strand RNA is more stable; and the like. The advantages of shRNA are such that: treatment through long-term suppression of gene expression can be achieved by producing a vector which can transcribe shRNA within a cell and introducing such a vector into the cell; and the like.

The siRNA or shRNA to be used in the present invention which can suppress the expression of the ITCH, AHCY, DYNLRB1, MAP1LC3A, PIGU, TP531PN2, NCOA6, HMG4L, or ASIP1 gene through RNAi, may be chemically synthesized in an artificial manner, and may also be produced through in vitro RNA synthesis using DNA of a hairpin structure in which a sense strand DNA sequence and an antisense strand DNA sequence are linked in opposite directions, with a T7 RNA polymerase. In the case of in vitro synthesis, antisense and sense RNAs can be synthesized from a template DNA using the T7 RNA polymerase and a T7 promoter. After in vitro annealing thereof, transfection of the resultant RNA into cells induces RNAi to suppress the expression of a target gene. Here, for example, transfection of such RNA into cells can be carried out by a calcium phosphate method or a method using various transfection reagents (such as oligofectamine, lipofectamine, and lipofection).

The abovementioned siRNA and shRNA are also useful as cell growth suppressing agents. The administration method of the cell growth suppressing agent of the present invention may include oral administration, parenteral administration (such as intravenous administration, intramuscular administration, subcutaneous administration, intradermal administration, transmucosal administration, intrarectal administration, intravaginal administration, local administration to affected area, and skin administration), and direct administration to affected area. The agent of the present invention, if used as a medical composition, may be mixed with a pharmaceutically acceptable additive as required. Specific examples of such a pharmaceutically acceptable additive include, but not limited to, an antioxidant, a preservative, a coloring agent, a flavoring agent, a diluent, an emulsifier, a suspending agent, a solvent, a filler, an extending agent, a buffer agent, a delivery vehicle, a diluting agent, a carrier, an excipient, and/or a pharmaceutical adjuvant.

The form of the pharmaceutical preparation of the agent of the present invention is not particularly limited, and examples thereof include a liquid agent, an injectable agent, and a sustained release agent. A solvent to be used for prescribing the agent of the present invention as the above pharmaceutical preparation may be either aqueous or non-aqueous.

Furthermore, the siRNA or shRNA serving as an active ingredient of the cell growth suppressing agent of the present invention can be administered in the form of a nonviral vector or a viral vector. In the case of a nonviral vector, there can be employed methods in which nucleic acid molecules are introduced using liposomes (such as a liposome method, an HVJ-liposome method, a cationic liposome method, a lipofection method, and a lipofectamine method), microinjection methods, methods in which nucleic acid molecules are transferred together with carriers (metal particles) into cells using a gene gun. If the siRNA or shRNA is administered in vivo using a viral vector, viral vectors such as a recombinant adenovirus and a recombinant retrovirus can be employed. Introduction of siRNA or shRNA gene into a cell or tissue can be achieved through introduction of DNA which expresses siRNA or shRNA into a detoxified DNA or RNA virus such as retrovirus, adenovirus, adeno-associated virus, herpes virus, vaccinia virus, poxvirus, poliovirus, Sindbis virus, Sendai virus, and SV40, followed by infection with the recombinant virus into the cell or tissue.

The dose of the cell growth suppressing agent of the present invention can be determined by those skilled in the art with a consideration of the purpose of administration, the disease severity, the age, weight, gender, and previous history of the patient, and the type of siRNA or shRNA serving as an active ingredient. The dose of siRNA or shRNA is not particularly limited, and examples thereof include about 0.1 ng/kg/day to about 100 mg/kg/day, and preferably about 1 ng/kg/day to about 10 mg/kg/day. RNAi effect is typically exerted for one to three days after the administration. Therefore, administration is preferably performed at a frequency of everyday to every third day. When an expression vector is used, the administration can be performed approximately once a week.

In the present invention, an antisense oligonucleotide can also be used as a cell growth suppressing agent. Antisense oligonucleotides to be used in the present invention are nucleotides that are complementary or hybridize to consecutive 5 to 100 nucleotide sequences within the DNA sequence of the ITCH, AHCY, DYNLRB1, MAP1LC3A, PIGU, TP531PN2, NCOA6, HMG4L, or ASIP1 gene. Such an antisense oligonucleotide may be either DNA or RNA, or may also be modified as long as its functions remain unaffected. The term "antisense oligonucleotide" used in this description includes not only oligonucleotides wherein all nucleotides corresponding to nucleotides composing a predetermined DNA or mRNA region are complementary to their counterparts, but also oligonucleotides that contain some mismatching nucleotides, as long as such oligonucleotides can stably hybridize to DNA or mRNA.

In addition, the antisense oligonucleotides may be modified. After appropriate modification, resulting modified antisense oligonucleotides will be hardly degraded in vivo. This enables more stable inhibition of the target. Examples of such modified oligonucleotide include S-oligo type (phosphorothioate-type), C-5 thyazole type, D-oligo type (phosphodiester-type), M-oligo type (methylphosphonate-type), peptide nucleic acid type, phosphodiester binding type, C-5 propinyl pyrimidine type, 2-O-propylribose, and 2'-methoxyribose type antisense oligonucleotides. Furthermore, such antisense oligonucleotide may also be an antisense oligonucleotide wherein at least some of the oxygen atoms composing phosphate groups are substituted with sulfur atoms or otherwise modified. Such an antisense oligonucleotide is particularly excellent in terms of nuclease resistance, water solubility, and affinity for RNA. As such an antisense oligonucleotide wherein at least some of the oxygen atoms composing phosphate groups are substituted with sulfur atoms or otherwise modified, an S-oligo type oligonucleotide can be enumerated.

The number of nucleotides in such antisense oligonucleotide is preferably 50 or less and more preferably 25 or less. Too large number of nucleotides results in increased effort and cost in oligonucleotide synthesis and lowered yields. Furthermore, the number of nucleotides of such antisense oligonucleotide is 5 or more and preferably 9 or more. A number of nucleotides of 4 or less is undesirable because of the resulting lowered specificity to a target gene.

Such antisense oligonucleotide (or a derivative thereof) can be synthesized by a usual method. For example, an antisense oligonucleotide or a derivative thereof can be easily synthesized using a commercially available DNA synthesizer (such as one produced by Applied Biosystems). It can be obtained by a synthesis method such as a solid-phase synthesis method using phosphoroamidite or a solid-phase synthesis method using hydrogen phosphonate.

When an antisense oligonucleotide is used as a cell growth suppressing agent in the present invention, it is generally provided in the form of a medical composition containing the antisense oligonucleotide and additive(s) for pharmaceutical preparation (such as a carrier and an excipient). The antisense oligonucleotide can be administered as a medicament to mammals including humans. The route of administration for such an antisense oligonucleotide is not particularly limited and may be either of oral administration or parenteral administration (such as intramuscular administration, intravenous administration, subcutaneous administration, peritoneal administration, transmucosal administration in the nasal cavity or the like, and inhalation administration).

The form of the pharmaceutical preparation of such an antisense oligonucleotide is not particularly limited. Examples of the pharmaceutical preparation for oral administration include tablets, capsules, fine granules, powders, granules, liquids, and syrups. Examples of the pharmaceutical preparation for parenteral administration include injections, infusions, suppositories, inhalants, transmucosal absorption systems, transdermal absorption systems, nasal drops, and ear drops. The form of a drug containing the antisense oligonucleotide, additive(s) to be used for the pharmaceutical preparation, a method for producing the pharmaceutical preparation, and the like can be appropriately selected by those skilled in the art.

The dose of the antisense oligonucleotide can be appropriately determined with a comprehensive consideration of the gender, age, and weight of the patient, the symptom severity, the purpose of administration such as prevention or treatment, and the presence/absence of other complication symptoms. The dose is generally 0.1 µg/kg of body weight/day to about 100 mg/kg of body weight/day, and preferably 0.1 µg/kg of body weight/day to about 10 mg/kg of body weight/day.

Furthermore, in the present invention, a loss-of-function type gene of the ITCH, AHCY, DYNLRB1, MAP1LC3A, PIGU, TP531PN2, NCOA6, HMG4L, or ASIP1 gene can also be used as a cell growth suppressing agent. The loss-of-function type gene refers to a mutated gene which causes loss of function of the corresponding gene. Specific examples thereof include genes which translate proteins lacking their original functions, generally called muteins, including those lacking at least one constituent amino acid(s), those having at least one constituent amino acid(s) replaced by other amino acid(s), and those added with at least one amino acid(s), within the amino acid sequence produced by the concerned gene.

When such a loss-of-function type gene is used as the cell growth suppressing agent, it can be produced by mixing the abovementioned gene serving as an active ingredient with a base that is commonly used for gene therapeutic agents. Moreover, when such a gene is incorporated into a viral vector, virus particles containing the recombinant vector are prepared, and are then mixed with a base that is commonly used for gene therapeutic agents.

As to the base, bases commonly used for injectable agents can be used. Examples thereof include: distilled water: salt solutions containing sodium chloride, a mixture of sodium chloride and mineral salts, or the like: solutions of mannitol, lactose, dextran, glucose, or the like: amino acid solutions of glycine, arginine, or the like: and mixed solutions having glucose solution with an organic acid solution or salt solution. Alternatively, these bases can also be prepared into injectable agents in the form of a solution, suspension, or dispersion, with use of auxiliary agents such as an osmoregulator, a pH adjuster, a vegetable oil, and a surfactant, in accordance with usual methods which are already known to those skilled in the art. These injectable agents can also be prepared in the form of a pharmaceutical preparation to be dissolved at the time of use, through operations such as powderization or lyophilization.

The form of administration of the loss-of-function allele may be either systemic administration such as usual intravenous administration and intraarterial administration, or local administration such as local injection and oral administration. Furthermore, administration may also take a combined form with catheterization, gene introduction technology, or surgical operation.

The administration dose of the loss-of-function type gene varies depending on the age and gender of the patient, the symptom, the administration route, the frequency of administration, and the dosage form. Generally, the daily dose for an adult is within a range of about 1 µg/kg of body weight to 1000 mg/kg of body weight, and preferably a range of about 10 µg/kg of body weight to 100 mg/kg of body weight, in terms of weight of recombinant gene. The frequency of administration is not particularly limited.

Moreover, the abovementioned various gene therapeutic agents of the present invention can also be produced by adding a gene into a suspension of liposomes prepared by a usual method, followed by freezing and subsequent thawing.

Examples of the method for preparing liposomes include a membrane shaking method, a sonication method, a reverse phase evaporation method, and a surfactant removal method. The suspension of liposomes is preferably subjected to sonication treatment before addition of a gene, so as to improve the efficiency of encapsulation of the gene. The liposomes having the gene encapsulated therein may be intravenously administered either directly or in the form of a suspension with water, physiological salt solution, or the like.

The cell growth suppressing agent of the present invention is useful as an anti-tumor agent. The term "anti-tumor" used herein has its broadest meaning which includes both of a preventive function of preventing generation, metastasis or implantation of tumor and a therapeutic function of suppressing the growth of tumor cells, regressing tumor to inhibit progress of tumor or improving the symptom. The term "anti-tumor" is not interpreted in a limited way.

Specific examples of cancer to be treated with the anti-tumor agent of the present invention include, but are not limited to, malignant melanoma, malignant lymphoma, lung cancer, esophageal cancer, gastric cancer, large bowel cancer, rectal cancer, colonic cancer, ureteral tumor, gallbladder cancer, bile duct cancer, biliary tract cancer, mammary cancer, liver cancer, pancreatic cancer, testicular tumor, maxillary cancer, lingual cancer, labial cancer, oral cavity cancer, pharyngeal cancer, laryngeal cancer, ovarian cancer, uterine cancer, prostate cancer, thyroid gland cancer, brain tumor, Kaposi's sarcoma, angioma, leukemia, polycythemia vera, neuroblastoma, retinoblastoma, myeloma, bladder tumor, sarcoma, osteosarcoma, myosarcoma, skin cancer, basal cell cancer, skin appendage carcinoma, metastatic skin cancer, and cutaneous melanoma. Preferably, the cancer is thyroid gland cancer.

(3) Method for Activating Cell Growth and Cell Growth Activating Agent

The present invention further provides a method for activating cell growth which comprises introducing in vitro a gene selected from among ITCH, AHCY, DYNLRB1, MAP1LC3A, PIGU, TP531PN2, NCOA6, HMG4L or ASIP1 gene, or a protein which is am expressed product of said gene into a cell, and a cell growth activating agent comprising said gene or protein.

When a gene selected from among the ITCH, AHCY, DYNLRB1, MAP1LC3A, PIGU, TP531PN2, NCOA6, HMG4L or ASIP1 gene is handled, cDNA obtained from a cultured cell in accordance with a technique known in the art or cDNA enzymatically synthesized via PCR method or the like may be used. When DNA is obtained via PCR, PCR is carried out using a human chromosome DNA or cDNA library as a template and a primer designed to be capable of amplifying the nucleotide sequence of interest. The PCR-amplified DNA fragment can be cloned into an adequate vector that is capable of amplification in an *E. coli* host or the like.

Methods for preparing a detection probe or primer for the gene selected from among the ITCH, AHCY, DYNLRB1, MAP1LC3A, PIGU, TP531PN2, NCOA6, HMG4L or ASIP1 gene and for cloning the target gene are known in the art. For example, such procedures can be implemented in accordance with a method described in Molecular Cloning: A laboratory Manual, $2^{nd}$ Ed., Cold Spring Harbor Laboratory, Cold Spring Harbor, N.Y., 1989, Current Protocols in Molecular Biology, Supplement 1 to 38, John Wiley & Sons (1987-1997), or the like.

At least one gene selected from among the ITCH, AHCY, DYNLRB1, MAP1LC3A, PIGU, TP531PN2, NCOA6, HMG4L or ASIP1 gene may be incorporated into a vector and may then be used in the form of a recombinant vector. A viral vector or an expression vector for an animal cell may be used, and the use of a viral vector is preferable. Examples of viral vectors include retrovirus vector, adenovirus vector, adeno-associated virus vector, baculovirus vector, vaccinia virus vector, and lentiviral vector. Use of a retroviral vector is particularly preferable for the following reasons. That is, after a host cell is infected with a retroviral vector, a virus genome is incorporated into a host cell chromosome, and a foreign gene incorporated into the vector may be expressed stably for a long period of time.

Examples of an expression vector for an animal cell include pCXN2 (Gene, 108, 193-200, 1991), PAGE207 (JP Patent Publication (Kokai) No. 6-46841 A (1994)), and a modified form of either thereof.

The aforementioned recombinant vector can be produced by introducing a vector into an adequate host for transformation and culturing the resulting transformant. When a recombinant vector is a viral vector, a host cell into which such vector is to be introduced is an animal cell that is capable of virus production. Examples thereof include COS-7 cell, CHO cell, BALB/3T3 cell, and HeLa cell. Examples of host cells for a retroviral vector include ΨCRE, ΨCRIP, and MLV. An example of a host cell for an adenoviral vector and an adeno-associated virus is the 293 cell obtained from the human embryonic kidney cell. A viral vector can be introduced into an animal cell by the calcium phosphate method, for example. When a recombinant vector is an expression vector for an animal cell, the *E. coli* K12 strain, HB101 strain, or DH5α strain can be used as a host cell into which such vector is to be introduced. A method of *E. coli* transformation is known in the art.

The obtained transformants are cultured in a medium under culture conditions that are suitable for each transformant. For example, *E. coli* transformants can be cultured in a liquid medium (pH: about 5 to 8) containing a carbon source, a nitrogen source, inorganic matter, and other substances that are necessary for growth. In general, culture is conducted at 15° C. to 43° C. for about 8 to 24 hours. In such a case, a recombinant vector of interest can be obtained by a common DNA isolation/purification technique after the completion of culture.

Animal cell transformants can be cultured in medium such as a 199 medium, MEM medium, or DMEM medium containing about 5% to 20% fetal bovine serum, for example. The pH level of a medium is preferably about 6 to 8. In general, culture is conducted at about 30° C. to 40° C. for about 18 to 60 hours. In such a case, virus particles containing recombinant vectors of interest are released in a culture supernatant. Thus, the recombinant vectors of interest can be obtained by concentrating and purifying the virus particles by cesium chloride centrifugation, polyethylene glycol precipitation, filter-concentration, or the like.

The cell growth activating agent of the present invention can be produced by mixing the aforementioned gene as an active ingredient with a base material that is usually used for a gene therapeutic agent. When the aforementioned gene is incorporated into a viral vector, viral particles containing a recombinant vector are prepared, and such viral particles are mixed with a base material that is commonly used for a gene therapeutic agent.

In order to mix the above-mentioned gene or protein as an active ingredient, a base material that is usually used for injections can be used. For example, distilled water, a salt solution of sodium chloride or a salt solution mixture of sodium chloride and an inorganic salt, a solution of mannitol, lactose, dextran, or glucose, an amino acid solution of glycine or arginine, or a mixed solution of an organic acid solution or salt solution with a glucose solution can be used. Alternatively, in accordance with a method known to persons skilled in the art, an adjuvant such as an osmotic regulator, a pH adjuster, vegetable oil, or a surfactant may be added to such base material to obtain an injection in the form of a solution, suspension, or dispersion. Such injection can also be prepared as a preparation to be dissolved before use via pulverization or lyophilization.

The administration route of the cell growth activating agent of the present invention may be systemic administration, such as general intravenous or intraarterial administration, or topical administration, such as topical injection or oral administration. Further, administration of the cell growth activating agent can be carried out in combination with catheterization, gene introduction, surgery, or the like.

The dose of the cell growth activating agent of the present invention varies in accordance with the age, sex, condition of a patient, route of administration, the number of times of administration, or dosage form. In general, the dose is about 1 µg/kg body-weight to 1,000 mg/kg body-weight, and preferably about 10 µg/kg body-weight to 100 mg/kg body-weight, per day per adult in terms of the weight of a recombinant gene. The number of times of administration is not particularly limited.

(4) Method for Detection of Tumor Using ITCH Gene

The detection method for selecting target tumor, to which the cell growth suppressing agent (antitumor agent) of the present invention can be applied, comprises a step of analyzing an ITCH gene in a specimen, using DNA or RNA comprising the entire or a part of the ITCH gene. The term "a part of the ITCH gene" is used herein to mean an oligonucleotide consisting of, for example, approximately 10 to 30 contiguous nucleotides in the nucleotide sequence of the ITCH gene. As a specimen, there can be used a tissue section, blood, lymph, sputum, lung wash solution, urine, feces, tissue culture supernatant, or the like, which are suspected to comprise tumor cells.

The aforementioned expression such as "detection for selecting target tumor to which the antitumor agent can be applied" is used to mean examination of the presence or absence of tumor in tissues or the like, on which the antitumor agent of the present invention effectively acts.

The detection for selecting tumor is carried out by analyzing an ITCH gene in a specimen, using DNA or RNA comprising the entire or a part of the ITCH gene as a primer or a probe. The term "to analyze an ITCH gene" is used herein to specifically mean detection of amplification or deletion of the ITCH gene in genomic DNA, or detection of the abnormality of the expression level of the gene.

In the case of using the aforementioned DNA or RNA as a primer, mutation of the ITCH gene can be detected, for example, by amplifying a partial sequence of DNA prepared from a specimen according to a PCR method using two types of selected primers and then confirming the presence thereof, or by confirming the sequence of an amplification product or the sequence of an amplification product that has been incorporated into various types of plasmid vectors.

On the other hand, the abnormality of the expression level of the ITCH gene can be detected by a Northern hybridization method or an RT-PCR (reverse transcription-polymerase chain reaction) method using a probe comprising the aforementioned RNA sequence.

(5) Detection Method for Selecting Tumor Using Antibody Against ITCH Protein, or Fragment Thereof A detection method for selecting target tumor, to which the cell growth suppressing agent (antitumor agent) of the present invention can be applied, comprises a step of analyzing the amount of an ITCH protein contained in a specimen, using an antibody against the ITCH protein, or a fragment of said antibody.

An antibody against the ITCH protein used in the present invention (hereinafter referred to as an "ITCH antibody") can be produced by an ordinary method using the entire or a part of ITCH protein as an antigen. A part of ITCH protein means a polypeptide consisting of, for example, at least 6, preferably at least approximately 8 to 10, and more preferably at least approximately 11 to 20 contiguous amino acids in the amino acid sequence of the ITCH protein as shown in SEQ ID NO: 2. As a method of preparing the entire or a part of ITCH protein used as an antigen, either a biological method or a chemical synthesis method may be applied.

A polyclonal antibody can be produced, for example, by sufficiently immunizing an animal such as a mouse, a guinea pig, or a rabbit with the aforementioned antigen via inoculating the antigen into the subcutis, muscle, abdominal cavity, vein, or the like of such animal several times, and then collecting blood from such animal, followed by separation of serum. A monoclonal antibody can be produced, for example, by preparing hybridomas via cell fusion between the splenic cells of the mouse immunized with the aforementioned antigen and commercially available mouse myeloma cells, and then producing the monoclonal antibody from a culture supernatant of the hybridomas or from the ascites fluid of the mouse to which the hybridomas have been applied.

Using the thus prepared antibody against ITCH protein or a fragment thereof, the expression level of an ITCH protein contained in a specimen can be measured. For such measurement, immunological methods such as immunoblotting, enzyme immunoassay (EIA), radioimmunoassay (RIA), a fluorescence antibody method or immunocytostaining, or a Western blotting method may be applied, for example. Herein, a fragment of the antibody against ITCH protein means a single chain antibody fragment (scFv) of the antibody, etc. In addition, as a specimen, there can be used a bone marrow sample, a tissue section, blood, lymph, sputum, lung wash solution, urine, feces, tissue culture supernatant, or the like, which are suspected to comprise tumor cells. When the thus measured expression level of the ITCH protein in the specimen is low, expression of the ITCH gene is suppressed in tissues or cells used as specimens, and thus a target tumor, to which the antitumor agent of the present invention can be applied, can be selected.

The present invention is hereafter described in greater detail with reference to the following examples, although the technical scope of the present invention is not limited to these examples.

EXAMPLES

Experiment Materials

As 14 types of ATC cell lines used (KTA-1, KTA-2, KTA-3, KTA-4, ARO, FRO, TTA-1, TTA-2, TTA-3, 8305C, 8505C, HTC/C3, TCO-1, and KHM/5M), cell lines established from clinical samples were used. These cell lines were cultured in a medium containing 100 U/ml penicillin, 100 μg/ml streptomycin and 10% fetal bovine serum. 116 clinical specimens of primary thyroid carcinoma were obtained from Ito Hospital. After the patients' consent had been secured and approval had been given from an ethics committee of the aforementioned organization, these clinical specimens were used.

Example 1

Amplification and Deletion of Gene Regions in ATC Cell Lines

In order to detect a novel gene alteration in anaplastic thyroid carcinoma, using genomic DNA prepared from the aforementioned 14 types of ATC cell lines, CGH array analysis was carried out employing MGC Whole Genome Array-4500 (Inazawa J., et al., Cancer Sci. 95, 559-563, 2004). Genome extracted from normal cells derived from thyroid gland was used as a target, and this genome was labeled with Cy5. Genomic DNA prepared from an anaplastic thyroid carcinoma cell line was used as test DNA, and this genomic DNA was labeled with Cy3.

A specific analysis method will be described below. Specifically, DpnII-digested genomic DNA (0.5 μg) was labeled with BioPrime Array CGH Genomic Labeling System (Invitrogen) in the presence of 0.6 mM dATP, 0.6 mM dTTP, 0.6 mM dGTP, 0.3 mM dCTP, and 0.3 mM Cy3-dCTP (anaplastic thyroid carcinoma cell line) or 0.3 mM Cy5-dCTP (normal cells). Cy3- and Cy5-labeled dCTPs were acquired from GE Healthcare. Either Cy3- or Cy5-labeled genomic DNA was added to ethanol in the presence of Cot-1 DNA (Invitrogen), so that it was precipitated. The precipitate was dissolved in 120 μl of a hybridization mixed solution (50% formamide, 10% dextran sulfate, 2×SSC (1×SSC; 150 mM NaCl/15 mM sodium citrate), 4% sodium dodecyl sulfate, pH 7.0). After 30 minutes of incubation at 37° C., the CGH array was set in a hybridization machine (GeneTAC; Harvard Bioscience), followed by 48 to 72 hours of hybridization. Subsequently, the CGH array was washed in a 50% formamide/2×SSC (pH 7.0) solution at 50° C. for 15 minutes and then washed in 2×SSC/0.1% SDS at 50° C. for 15 minutes. After air-drying, the CGH array was monitored for fluorescence derived from Cy3 and Cy5 using a GenePix 4000B scanner (Axon Instruments, CA, U.S.A.). The thus obtained results were analyzed using a GenePix Pro 6.0 imaging software (Axon Instruments, CA, U.S.A.). The average fluorescence intensity derived from Cy3 was adjusted to be the same as that of fluorescence intensity derived from Cy5, and the ratio of Cy3/Cy5 was determined.

When a genome has no abnormality, the resulting ratio becomes 1:1 (log 2 ratio=0). Determination was performed as follows. A ratio of 1.32 (or higher):1 (log 2 ratio is 0.4 or more) indicates the presence of genome amplification, and a ratio of 4 (or higher):1 (log 2 ratio is 2 or more) indicates the confirmation of significant amplification. A ratio of 0.75 (or lower):1 (log 2 ratio=−0.4 or less) indicates possible heterozygote deletion in the genome, and a ratio of 0.25 (or lower):1 (log 2 ratio=−2 or less) indicates an extremely high possibility of homozygote deletion in the genome. The results are shown in Tables 1 and 2.

TABLE 1

Loci of high-level amplification (log2 ratio >2.0) detected in ATC cell lines by array-CGH analysis using MCG Whole Genome Array-4500

| Locus No. | BAC | Locus* Chr. band | Position | n | Cell line Name | Possible candidate gene[b] | Number of known genes within each locus |
|---|---|---|---|---|---|---|---|
| 1 | RP11-124A11 | 1q41 | 213,712,056-213,886,235 | 1 | TTA-1 | | 3 |
| | RP11-5F19 | 1q41 | 213,843,888-214,005,804 | 1 | TTA-1 | | |
| | RP11-79H5 | 1q41 | 214,152,848-214,333,834 | 1 | TTA-1 | | |
| | RP11-45L21 | 1q41 | 215,048,055-215,223,099 | 1 | TTA-1 | | |
| | RP11-66M7 | 1q41 | 215,209,941-215,373,866 | 1 | TTA-1 | | |
| 2 | RP11-54L9 | 3q28 | 191,443,377-191,627,661 | 1 | TTA-1 | | 8 |
| | RP11-455C22 | 3q28 | 191,341,029-191,525,722 | 1 | TTA-1 | | |
| | RP11-88H6 | 3q28 | 192,493,851-192,676,936 | 1 | TTA-1 | | |
| 3 | RP11-51M22 | 7q31.2 | 115,628,304-115,790,622 | 1 | TTA-1 | | 1 |
| 4 | RP11-451O18 | 8p12 | 33,148,264-33,325,914 | 1 | 8305C | DUSP26, RNF122 | 5 |
| | RP11-258M15 | 8p12 | 33,641,086-33,802,158 | 1 | 8305C | | |
| | RP11-91P13 | 8p12 | 33,915,031-34,077,419 | 1 | 8305C | | |
| 5 | RP11-142F22 | 8q22.2 | 100,024,093-100,777,928 | 1 | KTA-3 | | 1 |
| 6 | RP11-89K10 | 8q24.21 | 127,636,847-127,799,456 | 1 | TTA-1 | MYC | 2 |
| | RP11-89L16 | 8q24.21 | 129,633,607-129,784,954 | 1 | TTA-1 | | |
| 7 | RP11-91M10 | 11q14.1 | 84,821,843-84,975,001 | 1 | KTA-3 | | 0 |
| 8 | RP11-134G19 | 11q22.2 | 101,600,032-101,600,600 | 1 | KTA-3 | YAP1, BIRC2, BIRC3 | 8 |
| | RP11-28124 | 11q22.2 | 101,722,105-101,886,737 | 1 | KTA-3 | | |
| | RP11-817J15 | 11q22.2 | 101,922,842-102,095,829 | 1 | KTA-3 | | |
| 9 | RP11-19G24 | 17q12 | 32,528,985-32,674,877 | 1 | ARO | | 1 |
| 10 | RP11-318N1 | 20q11.22 | 32,349,241-32,542,223 | 1 | 8305C | | 2 |

*Based on UCSC Genome Browser. March 2006 Assembly (http://genome.ucsc.edu/cgi-bin/hgGateway).
[b]Representative candidate oncogene located around BAC.

TABLE 2

Loci of homozygous deletion (log2 ratio <−2.0) delected in ATC cell lines by array-CGH analysis using MCG Whole Genome Array-4500

| Locus No. | BAC | Locus* Chr. band | Locus* Position | Cell line n | Cell line Name | Possible candidate gene[b] | Number of known genes within each locus |
|---|---|---|---|---|---|---|---|
| 1 | RP11-113D19 | 9p21.3 | 20,996,401-21,158,464 | 1 | TTA-1 | MTAP, CDKN2A, CDK2B | 23 |
|   | RP11-344A7 | 9p21.3 | 21,506,374-21,676,227 | 2 | TTA-1, TTA-3 |  |  |
|   | RP11-408N14 | 9p21.3 | 22,155,847-22,309,629 | 2 | TTA-2, TCO-1 |  |  |
|   | RP11-441I5 | 9p21.3 | 22,309,630-22,479,595 | 2 | TTA-1, TTA-2 |  |  |
|   | RP11-11J1 | 9p21.3 | 22,479,496-22,579,721 | 2 | TTA-1, TTA-2 |  |  |
|   | RP11-782K2 | 9p21.3 | 22,584,981-22,585,358 | 2 | TTA-1. TTA-2 |  |  |
|   | RP11-346N23 | 9p21.3 | 22,604,694-22,796,769 | 2 | TTA-1, TTA-2 |  |  |
|   | RP11-33O15 | 9p21.3 | 22,823,087-22,823,490 | 1 | TTA-1 |  |  |
|   | RP11-482I10 | 9p21.3 | 24,547,905-24,738,555 | 1 | TTA-1 |  |  |
| 2 | RP11-185J20 | 16q13.2 | 6,588,011-6,758,741 | 1 | ARO |  | 1 |
| 3 | RP11-61L1 | 16q23.1 | 77,344,719-77,345,302 | 1 | KTA-4 | WWOX | 1 |

*Based on UCSC Genome Browser. March 2008 Assembly (http:// genome.ucsc.edu/cgi-bin/hgGateway).
[b]Representative candidate humor suppressor located around BAC.

Amplification was found in 1q41, 3q28, 7q31.2, 8p12, 8q22.2, 8q24.21, 11q14.1, 11q22.2, 17q12, and 20q11. Among these mutations, alterations in the chromosomal regions other than 11q22.2 were discovered for the first time in the present invention.

In addition, homozygous deletion was found from 3 sites (9p21.3, 16q13.2, and 16q23.1) in 6 out of the 14 cell lines (ARO, KTA-4, TCO-1, TTA-1, TTA-2, and TTA-3). Of these, deletion of the 9p21.3 region comprising a CDKN2A/p16 gene was observed most frequently. Homozygous deletion of 16q23 comprising a WWOX gene that was assumed to be a cancer-suppressing gene was detected only in the KTA-4 cell line. Homozygous deletion was detected in a novel region 16q13.2 in the ARO cell line. High-level amplification was detected from 10 regions in 4 out of the 14 cell lines (ARO, KTA-3, TTA-1, and 8305C).

From these results, it is considered that malignant transformation of thyroid gland can be detected by detecting alterations existing in the chromosomal regions shown in Tables 1 and 2.

Moreover, among these regions, high-level amplification of 20q11.22 has not yet been reported to date. It was revealed that this region was moderately amplified (log 2 ratio=1.6: BACPR11-318N1) not only in 8305C cells but also in KTA-4 (FIG. 1A). Pathological and clinical significance of gene amplification in tumor is greatly associated with the therapy of the tumor. Thus, attention was drawn to the 20q11.22 region, and analysis was carried out.

Example 2

Narrowing Down of Amplification Regions in 8305C and KTA-4 Cells by FISH Analysis, and Analysis of Expression of Genes Constituted In order to narrow down the amplification region of 20q11.22, seven BACs mainly including RP11-318N1 and the BAC of the 20q11 region used as a control probe were subjected to FISH analysis according to an ordinary method (Inoue J., Otsuki T., Hirasawa A., et al., Am J. Pathol; 165: 71-81, 2004).

Figure 1B:
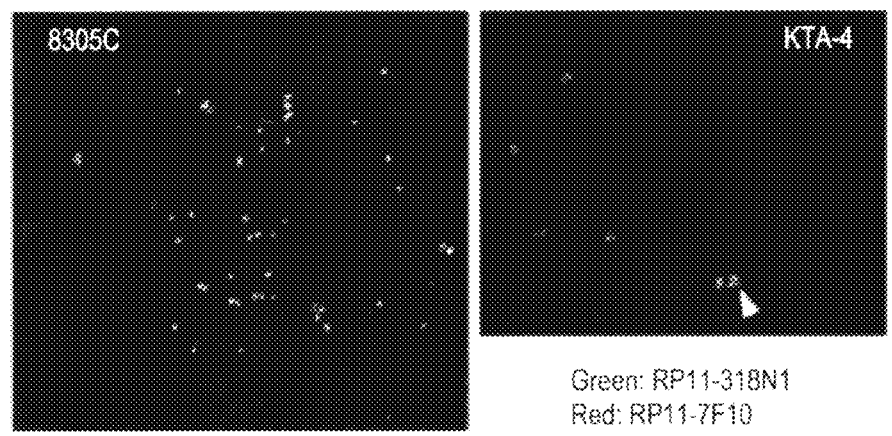
FIG. 1(B) shows the FISH analysis images of metaphase chromosomes produced from 8305C and KTA-4 cells. A BAC clone RP11-318N1 (green luminescence) was used as a probe. As a control probe, chromosome 20 BAC (RP11-7F10, 20p1.22; red luminescence) was used. The KTA-4 cells showed amplification due to a tandem repeat pattern (arrow portion), whereas clear amplification attended with double minute chromosomes (dmin) was detected in the 8305C cells.

Using the RP1-318N1 probe, a large number of signals attended with double minute chromosomes were found in the 8305C cells (FIG. 1B).

Figure 1C:
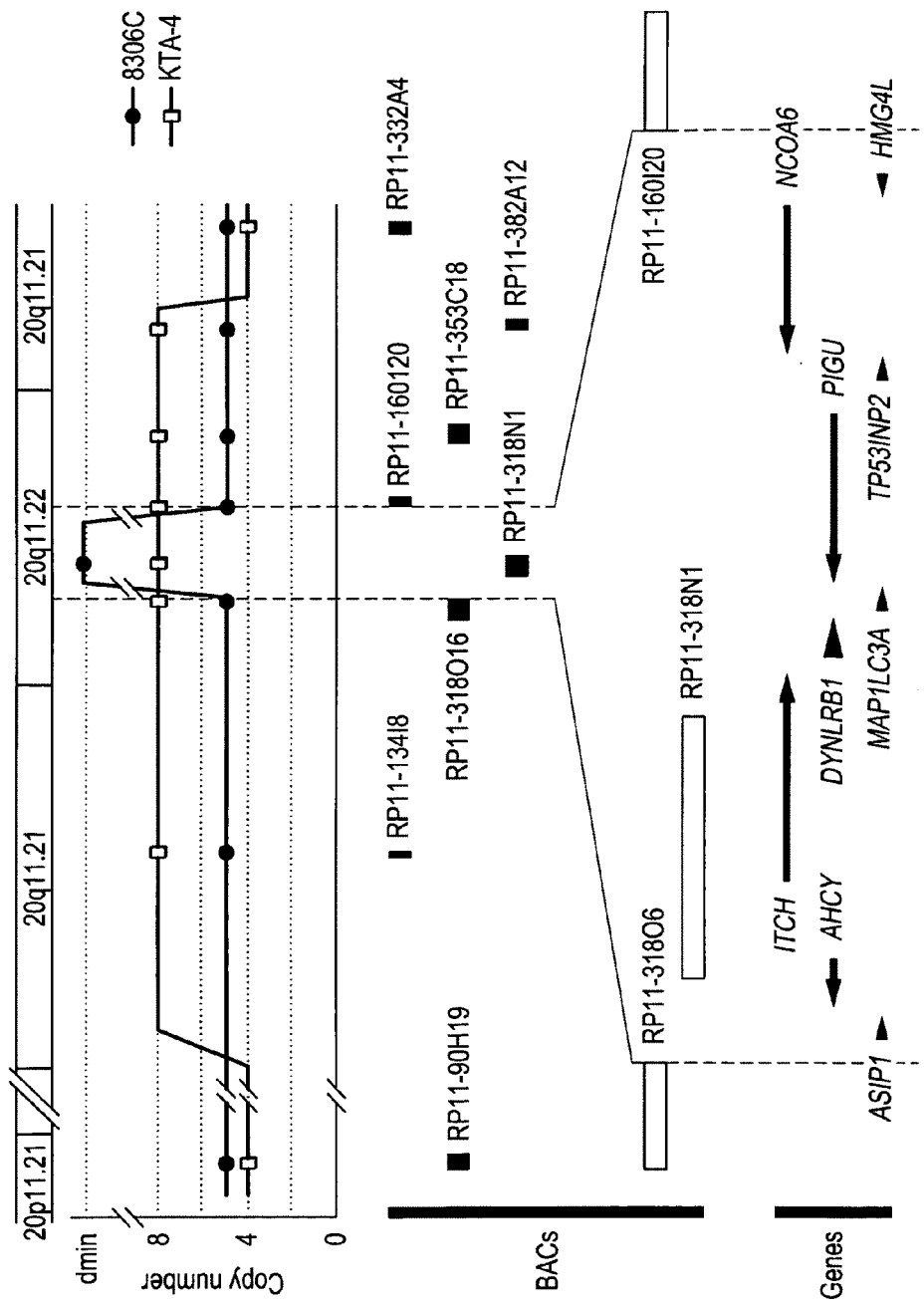
FIG. 1(C) shows a map of a region comprising 20q11.22 amplified in ATC cell lines. Eight BACs used in the FISH analysis are shown with black horizontal bars. The figure also shows 9 transcription products in the sequence. All markers and transcription products in SRO are disposed based on human genome database (ncbi.nlm.nih.gov and http://www.genome.ucsc.edu/).

On the other hand, 6 BACs (RP11-13418, 318O16, 318N1, 160I20, 353C18, and 382A12) detected 8 signals attended with a tandem repeat pattern in the KTA-4 cell line (FIG. 1B). From the results of the two types of cell lines, an amplification region as a target candidate was narrowed down to RP11-318N1, and through the human genome database (http://genome.ucsc.edu/), it was found that such amplification region has a size of approximately 0.6 Mb and comprises 9 genes consisting of ASIP1, AHCY, ITCH, DYNLRB1, MAP1LC3A, TP531PN2, PIGU, NCOA6, and HMG4L (FIG. 1C).

From the aforementioned results, it was found that malignant transformation of thyroid gland-derived cells can be detected by detecting increases in copy numbers of ASIP1, AHCY, ITCH, DYNLRB1, MAP1LC3A, TP531PN2, PIGU, NCOA6, and HMG4L.

Further, in order to clarify more preferred targets from among these target genes, the relationship between gene amplification and an expression state was tried to be determined.

Next, for the purpose of simple determination, a PCR reaction was performed on the 9 genes consisting of ASIP1, AHCY, ITCH, DYNLRB1, MAP1LC3A, TP53IPN2, PIGU, NCOA6, and HMG4L, which existed in the narrowed region. As a control of the expression level by RT-PCR, there was used GAPDH whose expression level had reportedly hardly changed depending on cell species or conditions. Total RNA was collected from each type of cells during the logarithmic growth phase, and cDNA was then produced by a common method. Primers specific for each gene (the nucleotide sequences of primers are shown in Table 3 (SEQ ID NOS: 1-18)) and conditions had been determined in advance, and a PCR reaction was then performed, followed by electrophoresis on 3% agarose gels.

TABLE 3

Supplementary Table S1 Primer sequences used in RT-PCR analysis

| Target gene | Forward primer | Reverse primer |
|---|---|---|
| ASIP | 5'-CAAACAGATCGGCAGAAAAGC | 5'-AAGAAGCGGCACTGGCAGGA |
| AHCY | 5'-CGCATCATCCTGCTGGCCGA | 5'-TCAGCCACTGCGTCATCCAG |

TABLE 3-continued

Supplementary Table S1 Primer sequences used in RT-PCR analysis

| Target gene | Forward primer | Reverse primer |
|---|---|---|
| DYNLRB1 | 5'-CACCACCACCCAGTATGC CAG | 5'-GTTGGATTCTGAATCACA ATCAGG |
| MAP1LC3A | 5'-TCCCGGACCATGTCAACA TG | 5'-CCATATAGAGGAAGCCGT CCT |
| PIGU | 5'-CTGTCCTGTGGCACCTCT GG | 5'-CTGTGCCATCCTTGGCGG T |
| NCOA6 | 5'-ATCCCAGGCCGAAGAAAC TC | 5'-TTACTTGGATTTTCTTCG CTTGG |
| TP53INP2 | 5'-CATGGGGTGAAGCCATCC CA | 5'-GACTCCTACTCAGGACTG CTG |
| HMG4L | 5'-GTGCAGACGTGCAGAGAA GA | 5'-CCTTAGCTGGTCCATAAT CCTTC |
| ITCH | 5'-TGCCATCTACCGTCATTA TGC | 5'-CCATGAGATCAGCAAATC CTC |

Figure 1D:
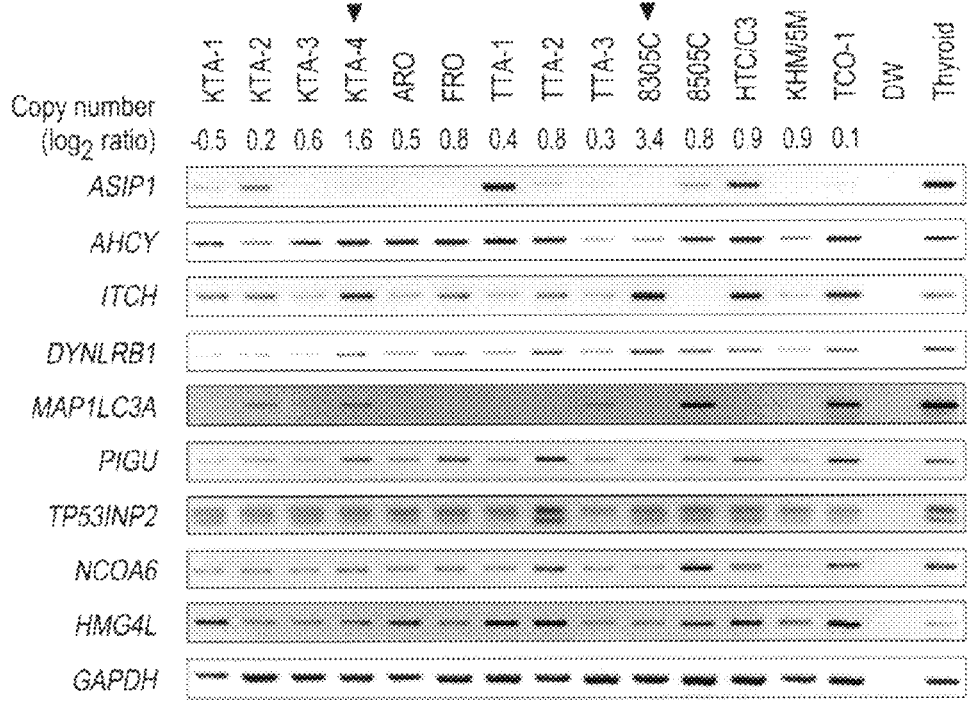
FIG. 1(D) shows expression of genes existing in the 20q11.22 region in ATC cell lines, which has been determined by RT-PCR. DW (distilled water) indicates a negative control. The amplified portion of 20q11.22 detected by array CGH is indicated with an arrow point. The copy number of the ATC cell lines correlated with the expression pattern of ITCH.

A gel image was obtained using LAS-3000 (Fuji Photo Film Co., Ltd.), and the image was then analyzed using Multi Gauge software (Fuji Photo Film Co., Ltd.) (FIG. 1D). The 14 cell lines were analyzed by a semi-quantitative RT-PCR method. As a result, it was found that the ITCH gene was clearly expressed at an excessive level in the 8305C cells and in the KTA-4 cells. Thus, it was found that the ITCH gene would become the most preferred target gene.

Example 3

Confirmation of Protein Expression Level of ITCH Gene in ATC Cell Lines

In order to confirm excessive expression of ITCH in 8305C and KTA-4, protein expression was confirmed by a Western blotting method using a specific antibody.

Figure 1E:
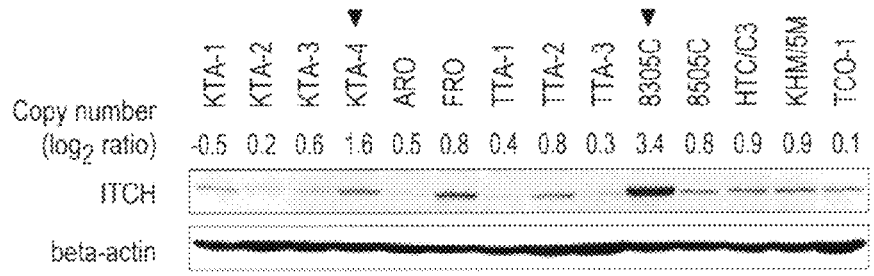
FIG. 1(E) shows the Western blotting analysis of ITCH proteins in ATC cell lines. The expression level of the ITCH protein also correlated with the copy number of this gene.

Specifically, each type of cells were dissolved in an RIPA buffer (10 mM Tris-HCl, 150 mM NaCl, 1 mM EDTA, 1% sodium deoxycholate, 0.1% SDS, 1% Triton X-100, pH 7.4) containing protease-inhibitor cocktail (Roche Diagnostics). Thereafter, a protein concentration was measured using BCA assay (Pierce Chemical), and 30 μg each of the cells was electrophoresed on SDS-polyacrylamide gels. The resultant was transferred on a difluoride membrane. After a primary detection with an anti-ITCH antibody (Santa Cruz Biotechnology) and an anti-β-actin antibody (Sigma) used as a control, a peroxidase-bound secondary antibody was used to develop color with an enhanced electrochemiluminescence system (Amersham), and it was then detected (FIG. 1E).

Figure 1F:
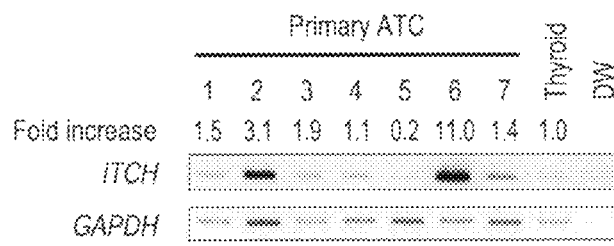
FIG. 1(F) shows the RT-PCR analysis of ITCH gene expression in 7 primary ATC specimens and normal thyroid tissues. Bands were quantified using LAS-3000 (manufactured by Fuji Photo Film Co., Ltd.) and Multi Gage software (manufactured by Fuji Photo Film Co., Ltd.). A numerical value obtained by dividing the expression level of ITCH in each specimen normalized with GAPDH by the expression level of ITCH in normal thyroid tissues is indicated as an increased amount.

Moreover, the expression level of ITCH mRNA in each of 7 specimens of primary anaplastic thyroid carcinomas was analyzed by an RT-PCR method. As a result, it was confirmed that ITCH mRNA was excessively expressed even in primary anaplastic thyroid carcinomas (FIG. 1F).

Example 4a

Excessive Expression of ITCH in Primary Thyroid Carcinomas

In order to examine the expression state of ITCH in primary thyroid carcinomas including ATC, 109 primary thyroid carcinoma specimens (ATC: 49 specimens; PTC: 25 specimens, PMC: 25 specimens; and adenomatous goiters: 10 specimens) were evaluated by immunohistochemical staining, in terms of the expression level of an ITCH protein.

Figure 2:
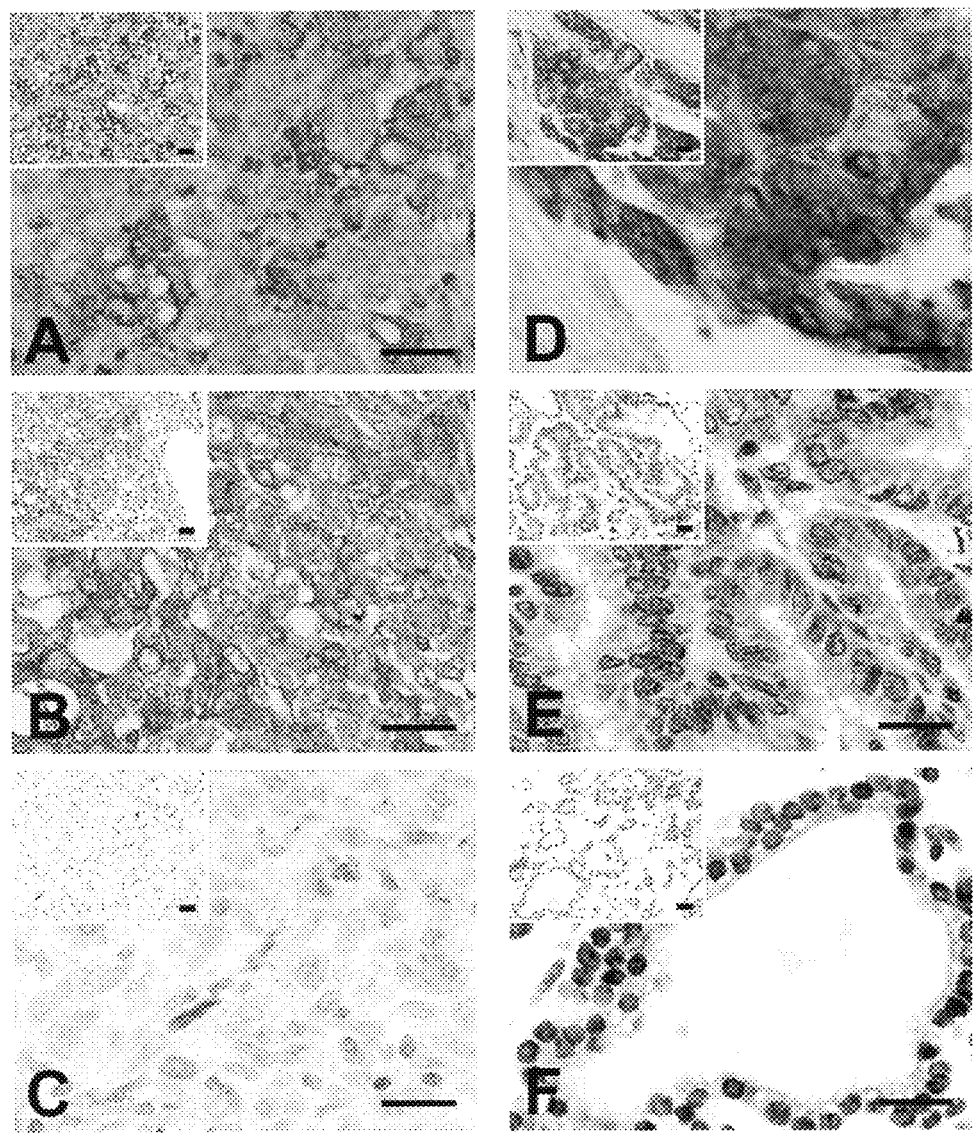
FIG. 2 shows examples of the ITCH immunostaining of primary thyroid carcinomas and benign thyroid tumors. (A) ATC (strength 3); (B) ATC (strength 2); (C) ATC (strength 0); (D) PMC (strength 3); (E) PTC (strength 2); and (F) thyroid tumor (strength 1). Based on the strength of immunostaining, the aforementioned carcinomas and tumors were classified into 4 strength levels. The horizontal bar indicates 20 μm.

As a specific method, a tissue section embedded in paraffin was fixed with formalin. A section placed on a glass slide coated with silane was subjected to deparaffinization and stepwise dehydration with ethanol. The antigen was subjected to a microwave pretreatment at 95° C. for 15 minutes in a 10 mM citrate buffer (pH 6.0), so that it was taken out. Endogenous peroxidase was inhibited using 5% hydrogen peroxide. Non-specific staining was inhibited using 2% standard pig serum. The slide was incubated at 4° C. overnight using an anti-human CTGF goat polyclonal antibody (L-20; 1:100 diluted; Santa Cruz Biotechnology). The slide was reacted with Histofine simple stain MAX PO (G) (Nichirei) at room temperature for 2 hours. The antigen-antibody reaction was visualized using 0.2% diaminobenzidine tetrahydrochloride and hydrogen peroxide. The slide was counterstained using Mayer's hematoxylin. The immunostaining pattern of ITCH is shown in FIG. 2, and the summary is shown in Table 4. The ATC specimens, PMC specimens, and PTC specimens were found to be positive in the immunostaining. On the other hand, thyroid tumors that were classified into benign tumors were not stained or were stained at an extremely weak level.

TABLE 4

| Tumor type | | n | Intensity (grade)[a] | Frequency (%) |
|---|---|---|---|---|
| Malignant tumor[b] | ATC | 49 | 3 | 3 (6.1%) |
| | | | 2 | 11 (22.4%) |
| | | | 1 | 27 (55.1%) |
| | | | 0 | 8 (16.3%) |
| | PTC | 25 | 3 | 0 (0%) |
| | | | 2 | 14 (56.0%) |
| | | | 1 | 11 (44.0%) |
| | | | 0 | 0 (0%) |
| | PMC | 25 | 3 | 1 (4.0%) |
| | | | 2 | 10 (40.0%) |
| | | | 1 | 14 (56.0%) |
| | | | 0 | 0 (0%) |
| Benign tumor | Adenomatous goiter | 10 | 3 | 0 (0%) |
| | | | 2 | 0 (0%) |
| | | | 1 | 9 (90.0%) |
| | | | 0 | 1 (10.0%) |
| Normal thyroid | | | 0 | |

[a]ICTH protein expression level was evaluated by immunohistochemical analysis as described in Materials and Methods.
[b]ATC, anaplastic thyroid carcinoma: PTC, papillary thyroid carcinoma; PMC, papillary microcarcinoma.

Example 4b

Oncogenic Activity in ATC Cells

In order to examine the effect of excessive expression of ITCH on the growth of ATC cells, a cell growth test was carried out after suppression of the expression of ITCH with specific siRNA.

Figure 3A:
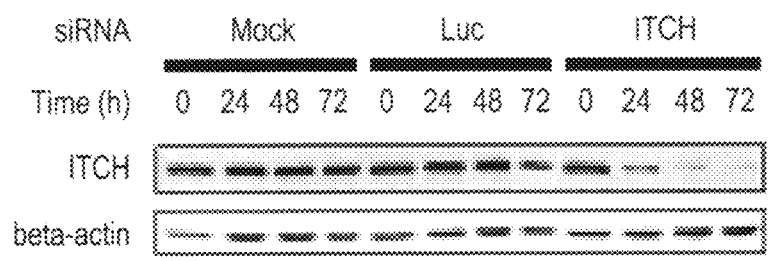
FIG. 3(A)-(C) show the effect of ITCH to suppress the growth of ATC cells. In comparison with si-RNA-Luc-introduced cells or only a solvent added, FIGS. 3(A) and (B) show the results obtained by performing Western blotting on 8305C cells (A) and KTA-4 cells (B), into which ITCH-specific siRNA (siRNA-ITCH) was introduced, and the growth curves thereof. Knock-down effect by siRNA was examined from 24 to 72 hours after gene transduction. The number of surviving cells 24 to 72 hours after the gene transduction was counted by a WST test method. The data show the average number obtained from 3 times of measurements. The symbol ※ indicates P<0.05 (statistical analysis by Mann-Whitney U method).
Figure 3A:
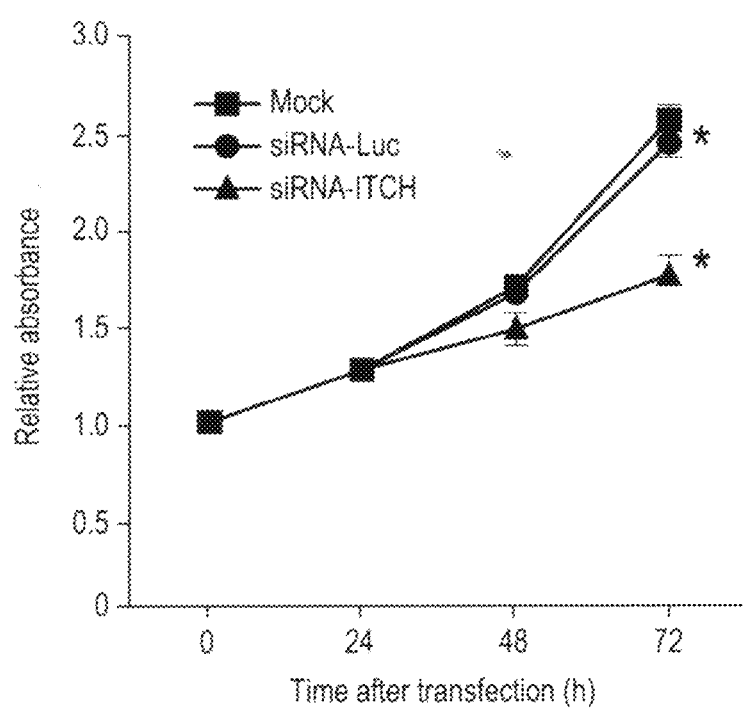
Figure 3B:
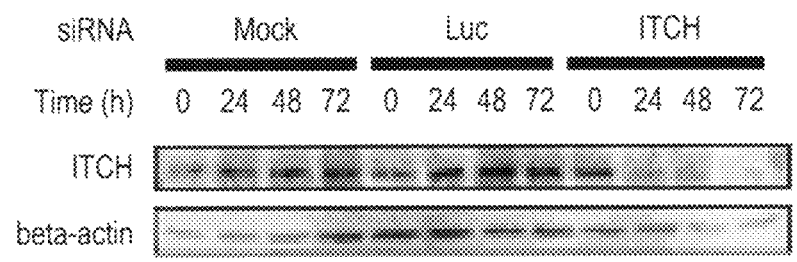
Figure 3B:
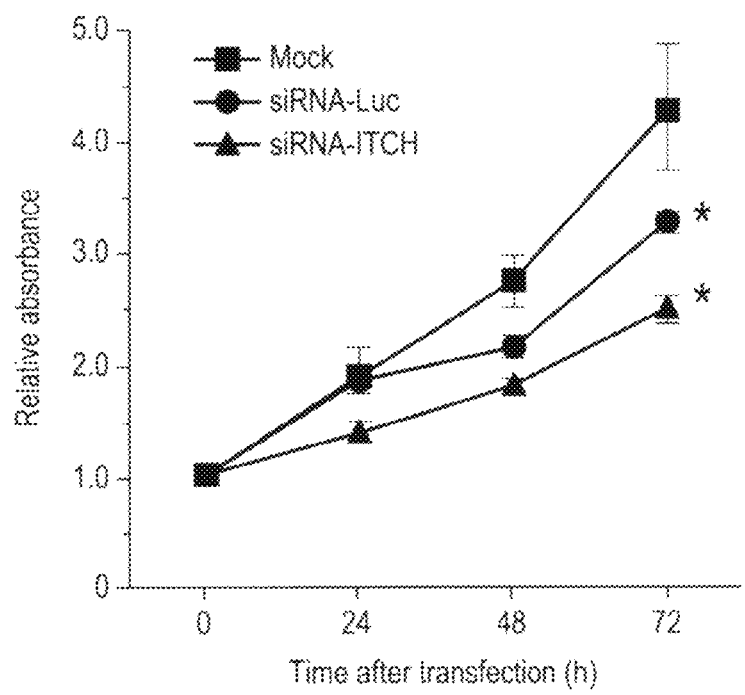

The siRNA corresponding to the ITCH gene was designed to be GGUGACAAAGAGCCAACAAGAG (SEQ ID NO: 19), and it was then purchased (from Sigma). Moreover, as control siRNA, CGUACGCGGAAUACUUCGA (SEQ ID NO: 20) that corresponded to a luciferase gene was purchased (from Sigma). The synthesized siRNA (10 nmol/L) was introduced into each ATC cell line, using Lipofectamine siRNA MAX reagent (Invitrogen) (by treating with production protocols). After introduction of the gene, the efficiency was analyzed by a Western blotting method in the same manner as that of Example 3. The number of surviving cells was measured by a water-soluble tetrazolium salt (WST) assay (Cell counting kit-8; Dojindo Laboratories). As a control, an anti-β-actin antibody was used. As predicted, in the 8305C and KTA-4 cells in which ITCH had been amplified/excessively expressed, the amount of an endogenous ITCH protein was suppressed by the ITCH-specific siRNA, 24 to 72 hours after the gene introduction, as compared with the case of using the non-specific siRNA control. This result was confirmed by a Western blotting method (FIGS. 3A and B).

Furthermore, each of the two above types of cell lines was seeded in a 24-well plate, and they were then transfected with the siRNA. Thereafter, the number of surviving cells was measured over time, using a water-soluble tetrazolium salt (WST) assay (Cell counting kit-o; Dojindo Laboratories), so as to examine the effect of ITCH on the cell growth (FIGS. 3A and B).

The growth of the 8305C cells was clearly suppressed by the ITCH-specific siRNA. The same results were obtained from the KTA-4 cells in which ITCH had been excessively expressed. However, the effect of ITCH to suppress the growth of the KTA-4 cells was smaller than in the case of the 8305C cells. Thus, it is considered that such cell growth-suppressing effect depends on the expression level of the ITCH protein. The effect of ITCH to suppress cell growth was 77% in the case of the 8305C cells and was 69% in the case of the KTA-4 cells.

Example 5

Analysis of Mode of Action of ITCH Gene Using Fluorescence-Activated Cell Sorting (FACS) Method In order to clarify the mode of action of ITCH on the growth of ATC cells, the cell cycle of 8305C cells into which ITCH-specific siRNA had been introduced and that of control cells were analyzed by FACS.

Specifically, the cells were treated with trypsin and were then fixed with a 70% ethanol solution overnight. Thereafter, the cells were treated with RNaseA (40 U/ml) for 30 minutes, and then with a PI solution of PBS buffer (20 g/ml) for 30 minutes. The amount of DNA in the cells was analyzed using FACSCaliber cytometer and Cell Quest software (both products manufactured by Becton-Dickinson). The experiment was carried out 3 times.

Figure 3C:
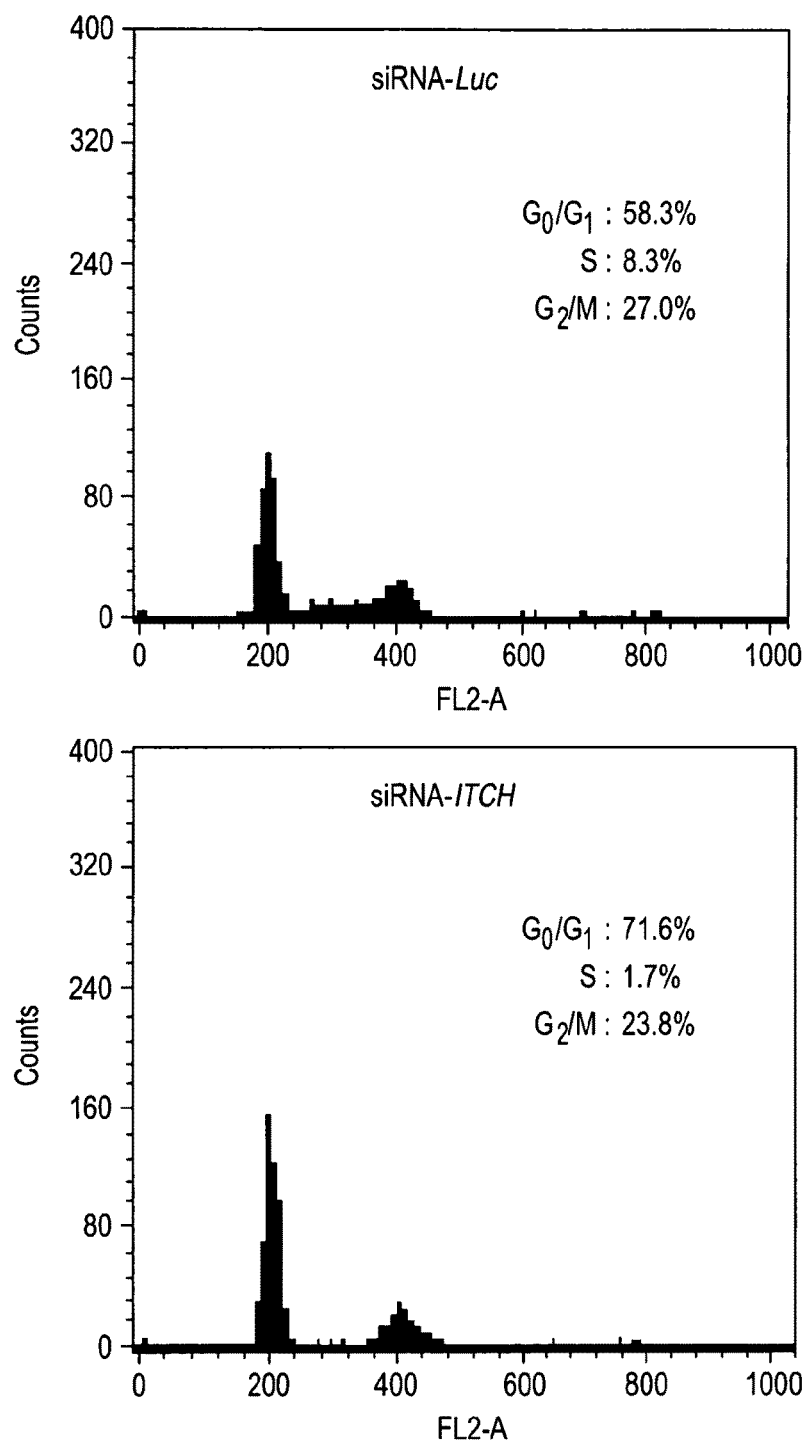

As a result of the analysis, it was found that, when the expression of ITCH was suppressed, G0/G1 increased, and S and G2/M decreased. This result clearly demonstrated that the cell cycle was terminated at a G1 phase (FIG. 3C).

Example 6

Confirmation of Effect of ITCH Gene to Promote Cell Growth

Figure 3D:
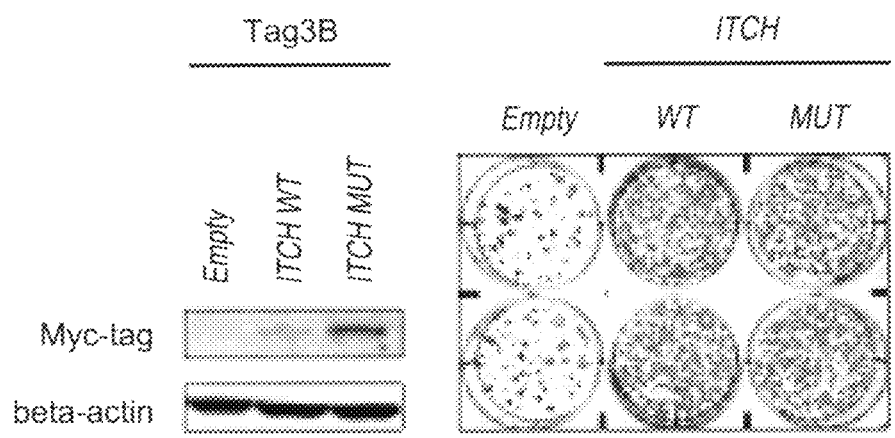
FIGS. 3(D) and (E) show a colony formation method using TTA-1 cells (D) and 8505C cells (E). Two plasmids for expressing the Myc tag of the ITCH gene (a wild type: pCMV-Tag3B-ITCH WT; a mutant type having-no ubiquitin-conjugating enzyme activity: pCMV-3Tag4-ITCH MUT) and an empty vector (pCMV-3Tag4-mock), into which no ITCH gene had been inserted, were introduced into cells in which the expression level of the ITCH gene was relatively low. Thereafter, the cells were allowed to grow for 3 weeks in the presence of G418 that was a neomycin agent. The transduction was confirmed by Western blotting (left), and a colony was formed as a result of the transduction (right).
Figure 3E:
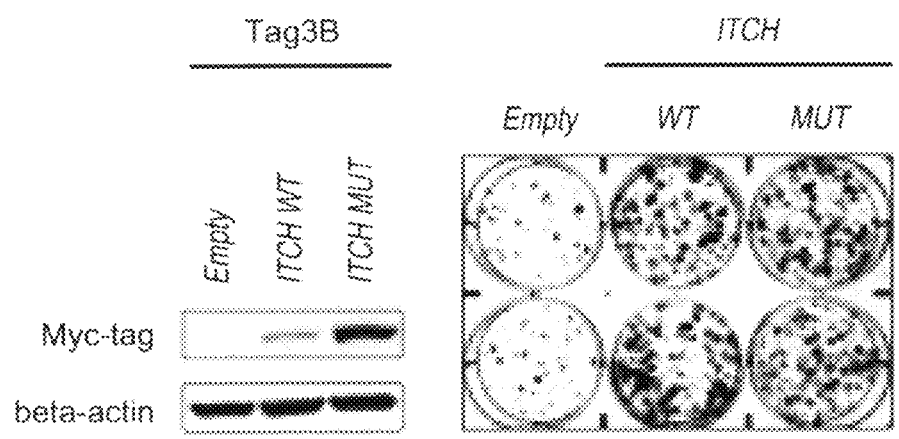

Based on the aforementioned results, whether or not the growth of the ATC cells is promoted by activation of expression of the ITCH gene was analyzed. First, there were constructed two plasmids for expressing the Myc tag of the ITCH gene (a wild type: pCMV-Tag3B-ITCH WT; a mutant type having no ubiquitin-conjugating enzyme activity: pCMV-Tag3B-ITCH MUT). These plasmids were produced by inserting the cDNA of ITCH WT or MUT amplified by RT-PCR into a pCMV-3Tag4 vector (Stratagene) such that the Myc tag could be matched with a translation frame. As a control, an empty vector in which no ITCH gene had been inserted was used (pCMV-Tag3B-mock). These expression plasmids were mixed with Lipofectamine 2000 (Invitrogen) used as a transfection reagent. Thereafter, TTA-1 cells or 8505C cells were transfected with the obtained mixture. Forty-eight hours later, the cells were recovered, and were then subjected to Western blotting using an anti-Myc antibody (Cell Signaling Technology), so as to confirm the expression of an ITCH protein (FIGS. 3D and E).

Further, 3 weeks after the transfection, the cells that had grown in the presence of G418 used as a neomycin agent were fixed with 70% ethanol, and they were then stained with crystal violet, so that they were counted. As a result, in comparison with the cells transfected with the empty vector, the number of colonies was significantly increased in the case of the cells transfected with pCMV-Tag3B-ITCH WT or MUT (FIGS. 3D and E). From this result, it became clear that the growth of the ATC cells can be promoted by activating the expression of the ITCH gene, and that such cell growth occurs in a manner independent from ubiquitin-conjugating enzyme.

CONCLUSION (1) As a result of the screening by an array CGH method, it was found that gene regions 1q41, 3q28, 7q31.2, 8p12, 8q22.2, 8q24.21, 11q14.1, 11q22.2, 17q12, 20q11, 9p21.3, 16q13.2, and 16q23.1 can be used as novel cancer markers for thyroid carcinoma.
(2) It was found that, among these gene regions, the 22q11 region and 9 genes (ITCH, AHCY, DYNLRB1, MAP1LC3A, PIGU, TP531PN2, NCOA6, HMG4L, and ASIP1) included therein can be used as more preferred cancer markers.
(3) As a result of confirmation by the combined use of the screening for a DNA amplification gene in cells derived from 14 types of anaplastic thyroid carcinomas with the expression analysis data, the ITCH gene was identified as a particularly preferred novel cancer marker.
(4) It was clarified that expression of the ITCH gene promotes the cell growth of thyroid carcinoma.

The invention claimed is:

1. A method for detecting an increased risk of anaplastic thyroid carcinoma in a human, which comprises:

a) detecting mRNA of an itchy homolog E3 ubiquitin protein ligase (ITCH) gene in a thyroid biopsy sample from the human by performing an RT-PCR method using primers consisting of SEQ ID NO: 17 and 18 and determining an increased level of mRNA in the sample as compared with a non-anaplastic thyroid carcinoma sample from a human;

b) detecting protein expression of an ITCH gene in the sample by performing an immunohistochemical method; and c) determining an increase risk of anaplastic thyroid carcinoma in the human when an increased level of mRNA and protein expression is detected.

* * * * *

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
```
caaacagatc ggcagaaaag c                                               21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
aagaagcggc actggcagga                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cgcatcatcc tgctggccga                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tcagccactg cctcatccag                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
caccaccacc cagtatgcca g                                               21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gttggattct gaatcacaat cagg                                            24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tcccggacca tgtcaacatg                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ccatatagag gaagccgtcc t                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ctgtcctgtg gcacctctgg                                                  20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
ctgtgccatc cttggcggt                                                   19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
atcccaggcc gaagaaactc                                                  20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ttacttggat tttcttcgct tgg                                              23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
catggggtga agccatccca                                                  20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gactcctact caggactgct g                                              21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gtgcagacgt gcagagaaga                                                20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
ccttagctgg tccataatcc ttc                                            23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tgccatctac cgtcattatg c                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ccatgagatc agcaaatcct c                                              21

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 19
ggugacaaag agccaacaag ag                                             22

```
<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 20
cguacgcgga auacuucga                                                19
```